United States Patent [19]

Nejigaki et al.

[11] Patent Number: 4,840,769
[45] Date of Patent: Jun. 20, 1989

[54] PROCESS FOR STERILIZING A FILTRATION DEVICE

[75] Inventors: Tatuo Nejigaki; Yoshimi Kakutani, both of Fuji, Japan

[73] Assignee: Asahi Kasei Kogyo Kabushiki Kaisha, Osaka, Japan

[21] Appl. No.: 850,610

[22] Filed: Apr. 11, 1986

[30] Foreign Application Priority Data

Apr. 18, 1985 [JP] Japan .................. 60-81347
Apr. 18, 1985 [JP] Japan .................. 60-81348
May 21, 1985 [JP] Japan .................. 60-107063

[51] Int. Cl.$^4$ .............................. A61C 2/06
[52] U.S. Cl. ......................... 422/26; 422/48; 210/636
[58] Field of Search ............ 422/26, 27, 44, 45, 422/48; 210/636

[56] References Cited

U.S. PATENT DOCUMENTS 4,176,156 11/1979 Asanuma et al. .......... 210/321.3
4,268,279 5/1981 Shindo et al. .............. 422/48
4,366,051 12/1982 Fischel ....................... 422/26

FOREIGN PATENT DOCUMENTS 2524079 12/1975 Fed. Rep. of Germany ........ 422/26
2446991 4/1976 Fed. Rep. of Germany ........ 422/26

OTHER PUBLICATIONS

Oda et al.; Chem. Econ. & Engineering Review; vol. 11, No. 12 (No. 124); 1979, pp. 36–40.

Primary Examiner—Benoit Castel
Attorney, Agent, or Firm—Birch, Stewart, Kolasch & Birch

[57] ABSTRACT

A process for sterilizing a filtration device which comprises employing therein a hollow fiber type module having hollow fibers of heat resistant polymer with a heat distortion temperature of 70° C. or higher under a load of 18.6 kg/cm$^2$ and with a pore diameter of less than 0.45 μm and having a difference in average linear expansion coefficient between the sealing material for fixing the end portions of the hollow fibers in the module case, at a temperature of 20°–121° C. of $7 \times 10^{-5}$/°C. or lower, and passing steam from the raw water side of the module to the filtrate side thereof, while withdrawing all or a part of the raw water and filtrate which partially fill the module or alternatively after withdrawal of raw water and filtrate.

5 Claims, 2 Drawing Sheets

PROCESS FOR STERILIZING A FILTRATION DEVICE

BACKGROUND OF THE INVENTION

1. Field of the Invention

The present invention relates to a process for sterilizing a filtration device, and more particularly to a process for the steam sterilization of a filtration device having a hollow fiber type module.

2. Description of the Prior Art

As methods for sterilizing a semipermeable membrane filtration device, the method of using chemicals such as sodium hypochlorite or a heating sterilization method utilizing hot water at a temperature of about 90° C. have been employed.

In the method where chemicals are used, there has been employed the sterilization method in which a sterilizer such as sodium hypochlorite, hydrogen peroxide and formalin etc. is filtered through a semipermeable membrane disposed in a semipermeable membrane filtration device from the raw water side of the device. However, according to this method, if air remains within the pipelines due to the structure of the pipelines or instruments, some portions thereof are not filled with the sterilizer and thus are insufficiently sterilized.

On the other hand, according to the hot water sterilization method, even when sterilization is effected with hot water at a temperature of about 90° C., heat resistant spores which cannot be killed at about 90° C. may sometimes exist, or there may be air or dead space remaining in the filtrate pipelines, whereby such portions cannot be effectively replaced with hot water thereby producing an insufficient sterilzing effect.

Further, after sterilization is performed with a sterilizer as described above, it is necessary to wash out the sterilizer. For this purpose a thorough rinsing with water is required to be performed, whereby not only a long time is required, but also the waste water must be disposed of.

In the prior art, no filtration device is known which uses a hollow fiber type membrane module which can with stand steam sterilization. This is because the hollow fiber type module generally employs hollow fiber membranes fixed at both ends onto a module case with a sealing material, whereby the membrane properties are lowered under the high temperature and high pressure conditions of steam sterilization or leaks may occur at the sealed portions.

SUMMARY OF THE INVENTION

An object of the present invention is to provide a process for sterilizing a filtration device which requires no rinsing with water after sterilization and yet can be sterilized at a high temperature without fear of secondary contamination.

Namely, the present invention relates to a process for sterilizing a filtration device which comprises employing a hollow fiber type module having hollow fibers of heat resistant polymer with a heat distortion temperature of 70° C. or higher under a load of 18.6 kg/cm² and with a pore diameter of less than 0.45 μm and having a difference in average linear expansion coefficient between the sealing material for fixing the end portions of the hollow fibers and the module case, at a temperature of 20°–121° C. of $7 \times 10^{-5}$/°C. or lower, and passing steam from the raw water side of the module to the filtrate side thereof, while withdrawing all or a part of the raw water and filtrate in the module or alternatively after the withdrawal of the raw water and filtrate.

DETAILED DESCRIPTION OF THE INVENTION

The filtration device which is employed in the present invention has a hollow fiber type module for ultrafiltration or microfiltration.

The hollow fiber membrane which can be employed in the module is made from a heat resistant polymer having a heat distortion temperature of 70° C. or higher under a load of 18.6 kg/cm². The heat distortion temperature is measured according to ASTM D648. If the heat distorton temperature is lower than 70° C., the membrane will be deformed during steam sterilization, whereby the membrane properties may become deteriorated or the membrane may be destroyed making it no longer usable. The membrane material may be made of materials having a heat distortion temperature of 70° C. or higher under a load of 18.6 kg/cm², and include, for example, polyvinylidene fluoride, polypropylene, polyphenylene oxide, ethylene-tetrafluoroethylene copolymer, polysulfone, polyethersulfone and others.

Further, the hollow fiber membrane used in the module has a pore diameter of less than 0.45 μm. The pore diameter is defined as the maximum particle size which can pass through the membrane. The membrane whose pore diameter is 0.45 μm or more cannot be employed in the present invention because fungi can easily pass through the membrane. The pore diameter of 0.2 μm to 1 nm is preferred.

The hollow fiber membrane which is used in the present invention can be prepared according to various methods. As the method for preparation of the membrane, it is possible to use the methods used in the preparation of ultrafiltration membranes and microfilters generally known in the art such as the micro-phase separation method, the stretching method and the extraction method.

Figure 1:
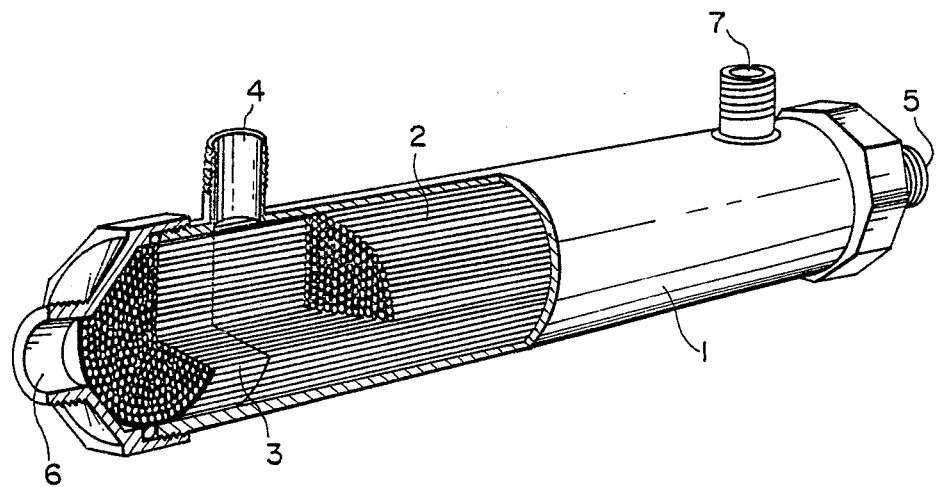
FIG. 1 shows the structure of a typical hollow fiber type module which can be used in the present invention.

An exemplary hollow fiber type module which can be used in the present invention is shown in FIG. 1. The module comprises a module case 1, a plurality of hollow fibers 2 and a sealing material 3 for fixing the end portions of hollow fibers 2 in the case 1. Element 4 is a filtrate outlet element, 5 is a raw water inlet, element 6 is a concentrated raw water outlet and a steam inlet and element 7 is a condensed water outlet. The difference of the average linear expansion coefficient between the sealing material and the material of the module case at between 20° C. and 121° C. must be $7 \times 10^{-5}$/°C. or lower. If the difference of the average linear expansion coefficient is more than $7 \times 10^{-5}$/°C., a seal keak will occur at the end portions when the module mounted in the filtration device is subjected to in-line sterilization with steam of 121° C.

The average linear expansion coefficient (β) between 20° C. and 121° C. is defined as follows:

$$\beta \, [1/°C.] = \frac{1}{l_o} \cdot \frac{l_{121} - l_{20}}{121 - 20}$$

wherein $l_0$, $l_{20}$ and $l_{121}$ are length at 0° C., 20° C. and 121° C., respectively.

Figure 2:
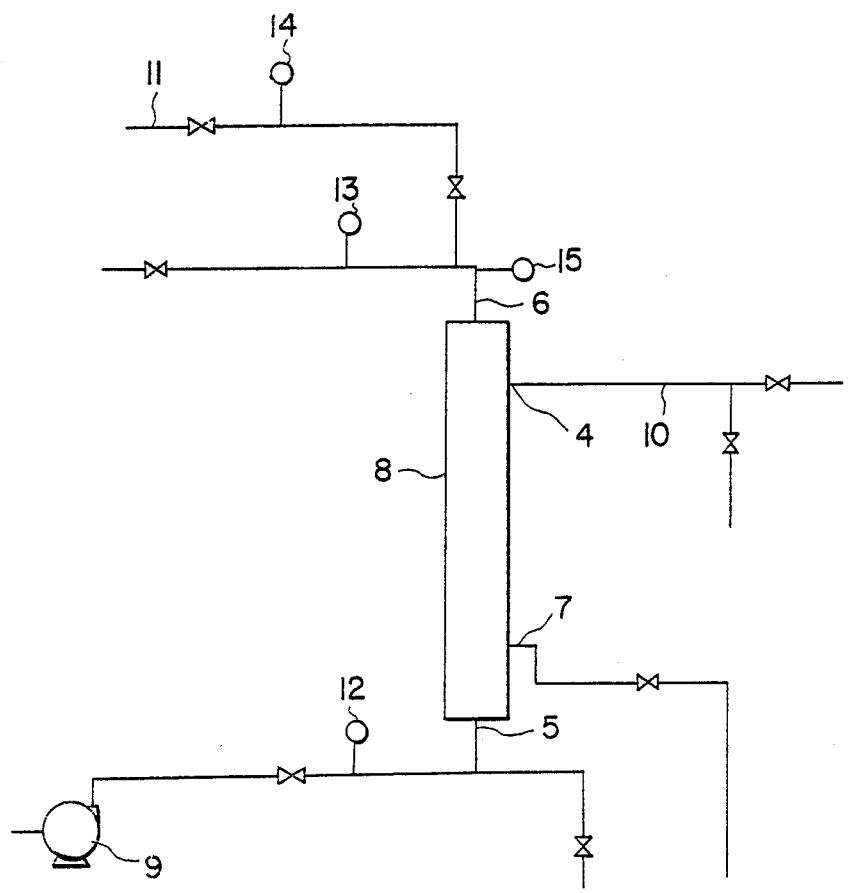
FIG. 2 shows an outline of a typical filtration device in which the hollow fiber type module is used.

This hollow fiber type module was mounted in a filtration device for removal of microorganisms from raw water as shown in FIG. 2. Element 8 is a hollow fiber type module, 9 is a feed pump of raw water, 10 is a filtrate pipeline, 11 is a steam feeding pipeline, 12, 13 and 14 are manometers and 15 is a thermometer.

The filtration device having the hollow fiber type module is sterilized by passing steam from the raw water side of the module to the filtrate side thereof, while withdrawing all or a part of the raw water and filtrate in the module or alternatively after withdrawal of the raw water and filtrate.

As the steam, a high temperature steam is generally used for enhancing the sterilization effect, but steam having a temperature of 121° C.~125° C. is usually employed with steam of 121° C. being preferred. The sterilization is usually conducted for 0.5 to one hour. The steam pressure which can be applied ranges from 1 to 1.5 kg/cm² G.

The steam sterilization of the present invention can be carried out at any time, for example, before filtration, during filtration and after filtration.

After passage of steam, the pressure at the sterilized portion becomes lowered due to the condensation of steam. Accordingly, if the device is left to stand as such, the pressure will become lower than atmospheric pressure, whereby unsterilized environmental air may leak into the system through the joints of the pipelines and the sterilization effect cannot be maintained.

To maintain the sterilization effect, especially on the filtrate side of the device, it is necessary to prevent the filtrate side from developing a negative pressure. As the method for prevention, the method in which water is introduced into the filtrate side through the memberane from the raw water side to fill the filtrate side with water can be employed. The water used for prevention of negative pressure preferably has a temperature of 80° C. or higher for alleviating the thermal shock on the hollow fiber type module.

Further, the method in which a sterilized gas is introduced into the filtrate side after the passage of steam can also be employed. The pressure of the gas introduced may be less than 1 kg/cm² and is preferably around 0.5 kg/cm². Under a pressure of 1 kg/cm² or higher, the performances of the filtration membranes will be lowered. As the gas to be introduced, there may be employed air, nitrogen, oxygen, helium and others.

According to the steam sterilization process of the present invention, it has become possible to sterilize internally the filtration device with steam at high temperature. Therefore, complicated steps such as rinsing with water after sterilization or disposal of the chemical solution after a sterilization as required in the prior art methods by use of a sterilizer are no longer necessary. Further, since the steam of high temperature used for sterilization is passed from the raw water side to the filtrate side through the hollow fiber membrane, sterilization can be surely effected on the filtrate side, including pipelines connected with the module.

Further, surer sterilization can be practiced as compared with heat sterilization with hot water of the prior art because the module used in the present invention has a high heat resistance.

Further, because the filtrate side is prevented from developing a reduced pressure with hot water or a sterilized gas after steam sterilization, the sterilized state can be maintained without contaminaton with environmental air.

The following examples illustrate the present invention in more detail, but they are given for illustrative purposes only and are not to be construed as limiting the present invention.

The number of living microorganisms in the filtrate in the Examples was counted by the following method.

1000 ml of filtrate was filtered by Bacteriological Monitor (Trade name; MILLIPORE Corp.). Then, M-TGE medium was fed to a Bacteriological Monitor and cultivation was carried out at 33° C. for 48 hours. The number of colonies on the surface of a filter of the Monitor was counted as the number of living microorganisms in 1000 ml of the filtrate.

EXAMPLE 1

As a hollow fiber type module, the module having about 2400 polysulfone hollow fiber membranes for ultrafiltration with a pore diameter of 5 nm, which were fixed in a polysulfone case at the end portions thereof with a sealing material of an epoxy resin was employed. The heat distortion temperature under 18.6 kg/cm² of the polysulfone resin constituting the hollow fiber membranes was 174° C. The average linear expansion coefficients at temperatures between 20° C. and 121° C. of the module case and the sealing material were $7 \times 10^{-5}/°C$. and $13 \times 10^{-5}/°C$., respectively, and the difference between both was $6 \times 10^{-5}/°C$.

Filtration was performed for two weeks in an ordinary manner by uses of the filtration device mounting module and then steam sterilization was applied to the device. The process of steam sterilization consisted of first stopping the feed pump 9, and introducing steam of 1.2 kg/cm² from the steam inlet 6 while discharging the condensed water from the condensed water outlet 7, the filtrate outlet 4 and the raw water inlet 5, thereby filling the module and filtrate pipelines with steam.

After this steam sterilization was carried out at about 121° C. for 30 minutes, the introduction of the steam was discontinued. Then, before the filtrate side develops a negative pressure, hot water heated to 80° C. was introduced from the raw water inlet to fill the filtrate side with hot water.

After this steam sterilization operation, filtration was performed again in the usual manner, but no seal leak of the module was found to be generated. Also, no living microorganism was found in 1000 ml of the filtrate after running for 2 weeks after the steam sterilization.

EXAMPLE 2

The same module as Example 1 except that microfilters of ethylene-tetrafluoroethylene copolymer (ETFE) having a pore diameter of 0.1 μm were used as the hollow fiber membranes. The heat distortion temperature under 18.6 kg/cm² of ETFE was 74° C. The steam sterilization of the filtration device mounting module was conducted in the same manner as Example 1.

After steam sterilization, filtration was carried out in a usual manner. Two weeks after the steam sterilization, no living microorganism was found at all in 1000 ml of the filtrate. Also, no seal leak was generated in the module.

EXAMPLE 3

The same filtration device as Example 1 was used except that a sterilized air feeding means was provided and filtration was carried out for two weeks in the usual manner. Then, the steam sterilization was applied to the device in the same manner as Example 1. After steam sterilizatin was carried out at about 121° C. for 30 minutes, the feeding of steam was discontinued and, before the filtrate side developed a negative pressure, air was introduced from a part of the filtrate pipelines to the filtrate side through a filter having a pore diameter of 0.2 μm for the removal of microorganisms from the air at a pressure of 0.5 kg/cm$^2$ until the filtrate side becomes 100° C. or lower. Then, the introduction of air was stopped and raw water was introduced from the raw water inlet to the module. The raw water was passed through membranes to replace the air in the filtrate side with filtrate, and again filtration was started. The living microorganism in 1000 ml of the filtrate, after two weeks of running after start-up was found to be zero, and there was no seal leak at the sealed portions of hollow fiber membrances.

When negative pressure prevention was practiced similarly by changing the pressure of the air to 1 kg/cm$^2$, there was observed a phenomenon that the water permeability of the hollow fiber membranes in the subsequent usual running was lowered by 5%, while it was within 1% when negative pressure prevention was practiced with the use of pressurized air at 0.5 kg/cm$^2$.

COMPARATIVE EXAMPLE

The same hollow fiber type module as Example 1 except that a stainless steel module case used was. The average linear expansion coefficients at temperatures between 20° C. and 121° C. of the module case and the epoxy resin were $2 \times 10^{-5}$/°C. and $13 \times 10^{-5}$/°C., with its difference being $11 \times 10^{-5}$/°C. By employing the filtration device mounting this module, the same filtration and steam sterilization as Example 1 were carried out.

After the steam sterilization, filtration was performed again. Two weeks after the steam sterilization, the number of living microorganisms in the filtrate was 830 per 1000 ml and a seal leak was found to be generated as judged by the pressurized air test under 1 kg/cm$^2$.

EXAMPLE 4

The same module as Example 1 except that an epoxy resin containing 33 parts by weight of silica powder was used as a sealing material. The average linear expansion coefficients at temperatures between 20° C. and 121° C. of the module case and the sealing material $7 \times 10^{-5}$/°C. and $8 \times 10^{-5}$/°C., respectively, and the difference between both was $1 \times 10^{-5}$/°C.

By using the filtration device mounting the module, filtration and steam sterilization were carried out in the same manner as Example 1.

After the steam sterilization, filtration was carried out again. Two weeks after the steam sterilization, the number of living microorganisms in 1000 ml of the filtrate was zero, and no seal leak was found in the module.

What is claimed is:

1. A process for sterilizing a filtration device containing residual raw water and filtrate and having a raw water side and a filtrate side and which employs therein a hollow, fiber type filtration module comprising hollow fibers disposed in a module case, said hollow fibers having end portions which are fixed in said module case by a sealing material, said hollow fibers being made of a heat resistant polymer with a heat distortion temperature of 70° C. or higher under a load of 18.6 kg/cm$^2$ and containing a pore diameter of less than 0.45 μm and the sealing material having a difference in the average linear expansion coefficient between it and the material of the module case of $7 \times 10^{-5}$/°C. or lower, at a temperature of 20°–121° C., which comprises
    (i) discontinuing filtration,
    (ii) passing sterilizing steam from the raw water side of the module to the filtrate side thereof, after pushing out the raw water from the raw water inlet of the module and filtrate from the module, with said sterilizing steam and
    (iii) preventing the filtrate side of the filtration device from developing a negative pressure by introducing a fluid selected from the group consisting of water and a sterilized gas into the filtration device from a raw water side during the natural cooling which takes place after the steam sterilization has been completed.

2. The process of claim 1 wherein the hollow, fiber type filtration module is a fiber membrane made of a material selected from the group consisting of polyvinylidene fluoride, polypropylene, polyphenylene oxide, ethylene-tetrafluoro-ethylene copolymer, polysulfone, and polyethersulfone.

3. The process of claim 1 wherein the sterilizing steam has a temperature of 121° to 125° C. and a pressure of from 1 to 1.5 kg/cm$^2$.

4. The process of claim 1 wherein a sterilizing gas having a pressure of 0.5 to 1 kg/cm$^2$ is introduced and said sterilizing gas is a member selected from the group consisting of air, nitrogen, oxygen, and helium.

5. The method of claim 1 wherein the sealing material is an epoxy resin or an epoxy resin containing silica powder.

* * * * *

UNITED STATES PATENT AND TRADEMARK OFFICE
CERTIFICATE OF CORRECTION

PATENT NO. : 4,840,769
DATED : June 20, 1989
INVENTOR(S) : Nejigaki et al

It is certified that error appears in the above-identified patent and that said Letters Patent is hereby corrected as shown below:

<u>Claim 4</u>

Line 1, change "sterilizing" to --sterilized--

Line 3, change "sterilizing" to --sterilized--

Signed and Sealed this

Twenty-ninth Day of May, 1990

*Attest:*

HARRY F. MANBECK, JR.

*Attesting Officer*   *Commissioner of Patents and Trademarks*